United States Patent [19]
Keshaviah et al.

[11] Patent Number: 6,074,359
[45] Date of Patent: Jun. 13, 2000

[54] METHOD AND APPARATUS FOR A TIDAL OSCILLATING PULSE PERITONEAL DIALYSIS

[75] Inventors: Prakash R. Keshaviah, Plymouth, Minn.; Jim Ebben, Hudson, Wis.; Paul Emerson, Minnetonka, Minn.; Kazuo Kumano, Kanagawa-ken, Japan

[73] Assignee: Baxter International Inc., Deerfield, Ill.

[21] Appl. No.: 08/420,896

[22] Filed: Apr. 11, 1995

Related U.S. Application Data

[63] Continuation of application No. 08/223,806, Apr. 6, 1994, abandoned.

[51] Int. Cl.[7] .................................................. A61M 1/00
[52] U.S. Cl. ........................ 604/29; 210/645; 604/19
[58] Field of Search ................ 604/4–6, 19, 29; 210/646, 645; 128/213

[56] References Cited

U.S. PATENT DOCUMENTS

| | | | |
|---|---|---|---|
| 3,698,494 | 10/1972 | Gaudin | 177/118 |
| 4,649,759 | 3/1987 | Lee | 73/862.64 |
| 4,755,168 | 7/1988 | Romanelli | 604/34 |
| 4,796,644 | 1/1989 | Polaschegg | 604/4 |
| 5,141,493 | 8/1992 | Jacobsen | 210/646 |

FOREIGN PATENT DOCUMENTS

| | | |
|---|---|---|
| 0 028 371 | 10/1980 | European Pat. Off. . |
| 0 157 024 | 12/1984 | European Pat. Off. . |
| 4117964 | 4/1992 | Japan . |
| WO94/01193 | 1/1994 | WIPO . |

*Primary Examiner*—John G. Weiss
*Assistant Examiner*—Dennis Ruhl
*Attorney, Agent, or Firm*—Charles R. Mattenson; Paula J. F. Kelly; Robert M. Barrett

[57] ABSTRACT

An improved peritoneal dialysis method and system is provided. The method utilizes a tidal oscillating pulse peritoneal dialysis system. To this end, a system for providing peritoneal dialysis to a patient is provided. The system comprises a single catheter that is placed in the patient, a reservoir of dialysate having a volume greater than or equal to three liters, and a single pump for pumping the dialysate from the reservoir into and out of the patient.

13 Claims, 4 Drawing Sheets

METHOD AND APPARATUS FOR A TIDAL OSCILLATING PULSE PERITONEAL DIALYSIS

This application is a continuation of application Ser. No. 08/223,806, filed Apr. 6, 1994, now abandoned.

BACKGROUND OF THE INVENTION

The present invention relates generally to the treatment of end stage renal disease. More specifically, the present invention relates to methods and apparatus for performing peritoneal dialysis.

Using dialysis to support a patient whose renal function has decreased to the point where the kidneys no longer sufficiently function is known. Two principal dialysis methods are utilized: hemodialysis and peritoneal dialysis.

In hemodialysis, the patient's blood is passed through an artificial kidney dialysis machine. A membrane in the machine acts as an artificial kidney for cleansing the blood. Because it is an extracorporeal treatment that requires special machinery, certain inherent disadvantages exist with hemodialysis.

To overcome the disadvantages associated with hemodialysis, peritoneal dialysis was developed. Peritoneal dialysis utilizes the patient's own peritoneum as a semipermeable membrane. The peritoneum is a membranous lining of the abdominal body cavity. Due to good perfusion, the peritoneum is capable of acting as a natural semipermeable membrane.

Peritoneal dialysis periodically infuses sterile aqueous solution into the peritoneal cavity. This solution is called peritoneal dialysis solution, or dialysate. Diffusive and osmotic exchanges take place between the solution and the blood stream across the natural body membranes. These exchanges remove the waste products that the kidneys normally excrete. The waste products typically consist of solutes like urea and creatinine. The kidneys also maintain the levels of other substances such as sodium and water which need to be regulated by dialysis. The diffusion of water across the peritoneal membrane during dialysis is called ultrafiltration.

In continuous ambulatory peritoneal dialysis, a dialysis solution is introduced into the peritoneal cavity utilizing a catheter. An exchange of solutes between the dialysate and the blood is achieved by diffusion. Further removal is achieved by providing a suitable osmotic gradient from the blood to the dialysate to permit water outflow from the blood. This allows a proper acid-base, electrolyte and fluid balance to be achieved in the body. The dialysis solution is simply drained from the body cavity through the catheter.

Peritoneal dialysis raises a number of concerns including: the danger of peritonitis; a lower efficiency and therefore increased duration of dialysis hours compared to hemodialysis; and costs incurred when automated equipment is utilized.

A number of variations on peritoneal dialysis have been explored. One such variation is automated peritoneal dialysis ("APD"). APD uses a machine, called a cycler, to automatically infuse, dwell, and drain peritoneal dialysis solution to and from the patient's peritoneal cavity. APD is particularly attractive to a peritoneal dialysis patient, because it can be performed at night while the patient is asleep. This frees the patient from the day-to-day demands of continuous ambulatory peritoneal dialysis during his/her waking and working hours.

The APD sequence typically lasts for several hours. It often begins with an initial drain cycle to empty the peritoneal cavity of spent dialysate. The APD sequence then proceeds through a succession of fill, dwell, and drain phases that follow one after the other. Each fill/dwell/drain sequence is called a cycle. APD can be and is practiced in a number of different ways.

Continuous cycling peritoneal dialysis ("CCPD") is one commonly used APD modality. During each fill/dwell/drain phase of CCPD, the cycler infuses a prescribed volume of dialysate. After a prescribed dwell period, the cycler completely drains the liquid volume from the patient, leaving the peritoneal cavity empty or "dry." Typically, CCPD employs six fill/dwell/drain cycles to achieve a prescribed therapy volume.

After the last prescribed fill/dwell/drain cycle in CCPD, the cycler infuses a final fill volume. The final volume dwells in the patient through the day. It is drained at the outset of the next CCPD session in the evening. The final fill volume can contain a different concentration of dextrose than the fill volume of the successive CCPD fill/dwell/drain fill cycles the cycler provides.

Tidal peritoneal dialysis ("TPD") is another APD modality. Like CCPD, TPD includes a series of fill/dwell/drain cycles. Unlike CCPD, TPD does not completely drain dialysate from the peritoneal cavity during each drain phase. Instead, TPD establishes a base fill volume during the first fill phase and drains only a portion of this volume during the first drain phase. Subsequent fill and drain cycles infuse, then drain a small tidal volume under the base volume, except for the last drain phase. The last drain phase removes all dialysate from the peritoneal cavity.

Yet another variation of automated peritoneal dialysis is reciprocating peritoneal dialysis ("RPD") and/or semi-continuous peritoneal dialysis. In such systems, dialysis solution is infused into the peritoneal cavity and then, typically, on a continuous process basis a portion of the dialysis solution is sequentially drained, cleansed, and reinfused.

FIG. 1 illustrates a system of semi-continuous dialysis. The system was outlined by Di Paolo in "Acceleration of Peritoneal Dialysis With Single Device", 19 *Nephron* 271–277 (1977). A single needle 10 is used to infuse fluid from the sterile reservoirs 12, 14 into the patient where it dwells and then subsequently flows to drain 16. Inflow into the patient is achieved through a pump 18, while outflow is achieved by gravity.

U.S. Pat. No. 4,190,047 discloses a single catheter system that utilizes two pumps to alternate inflow and outflow of dialysate fluid. During the outflow cycle, fluid is passed through the blood path of the dialyzer where it is "cleaned" prior to the next inflow.

FIG. 2 sets forth a figure from U.S. Pat. No. 5,141,493. FIG. 2 illustrates the three loop system of the '493 patent wherein dialysate is reciprocated into and out of the patient using a reversible pump (first loop) into a second loop. In the second loop, the dialysate passes through a dialyzer being regenerated by non-sterile dialysate flowing in the third loop. The difference between the '493 system and the earlier systems is that both regeneration and reciprocation are continuous.

All of the above investigators have reported increased small molecule clearance and high ultrafiltration with either a continuous flow or reciprocating type systems. Naturally, an advantage of this type is desirable. However, these prior systems are quite complex in their operation, set-up, and control. Therefore, a need exists for an improved peritoneal dialysis system based on a reciprocating and/or semi-continuous peritoneal dialysis.

SUMMARY OF THE INVENTION

The present invention provides an improved peritoneal dialysis method and system. The method utilizes a tidal oscillating pulse peritoneal dialysis system.

To this end, a system for providing peritoneal dialysis to a patient is provided. The system comprises a single catheter that is placed in the patient, at least one reservoir of dialysate having a volume of greater than or equal to three liters, and a single pump for pumping the dialysate into and out of the patient. In two alternative embodiments, the pump may be either a reversible roller pump or a personal cycler.

In an embodiment, the system further includes a force transducer coupled to the reservoir of dialysate for monitoring the amount of dialysate pumped into the patient.

In an embodiment, the system further includes a pressure detection system in communication with the pump.

In an embodiment, the system further includes means for vibrating the reservoir of dialysate during dialysis.

The present invention dialyzes the patient through a single catheter placed into the peritoneal cavity. At least one reservoir of dialysate having a volume of at least one and one half times the patient's fill volume, e.g., greater than or equal to three liters is also provided. The reservoir of dialysate is coupled in fluid communication with the catheter. Then, the dialysate is pumped into and out of the peritoneum using a single pump.

In an embodiment, the method of the present invention further includes the step of vibrating the reservoir of dialysate when pumping the dialysate into and out of the peritoneum.

An advantage of the present invention is that it provides an improved method for providing peritoneal dialysis to a patient.

A still further advantage of the present invention is that it provides a tidal oscillating pulse peritoneal dialysis that requires only a single pump.

Another advantage of the present invention that it provides a system that utilizes an external reservoir that participates in the peritoneal transport as if it were part of the peritoneal cavity. In addition, the present system is more efficient than multiple infusions since the inflow and outflow processes are eliminated.

Furthermore, an advantage of the present invention is that the fluid in the system is returned to the reservoir rather than the drain such that smaller quantities of fluid are used.

Moreover, an advantage of the present invention is that it provides smaller strokes allowing the flow rate to be high on both the inflow and outflow.

Still further, an advantage of the present invention is that it provides for greater mixing by breaking stagnant fluid layers in the peritoneal cavity.

Moreover, an advantage of the present invention is that no down time due to filling and emptying the peritoneal cavity exists. As a result, the same therapy obtained with prior systems can be obtained in less time or more therapy can be obtained in the same length of time or more therapy can be obtained in a given time with a smaller volume dialysis fluid.

Additional features and advantages of the present invention are described in, and will be apparent from, the detailed description of the presently preferred embodiments and from the drawings.

DETAILED DESCRIPTION OF THE PRESENTLY PREFERRED EMBODIMENTS

The present invention provides an improved method and system for providing peritoneal dialysis to a patient. Specifically, the present invention provides a tidal oscillating pulse peritoneal dialysis system. Pursuant to the system of the present invention, a single pump and fluid circuit, as well as a single catheter, can be utilized. Moreover, the system utilizes at least one reservoir having a volume greater than or equal to three liters.

Figure 1:
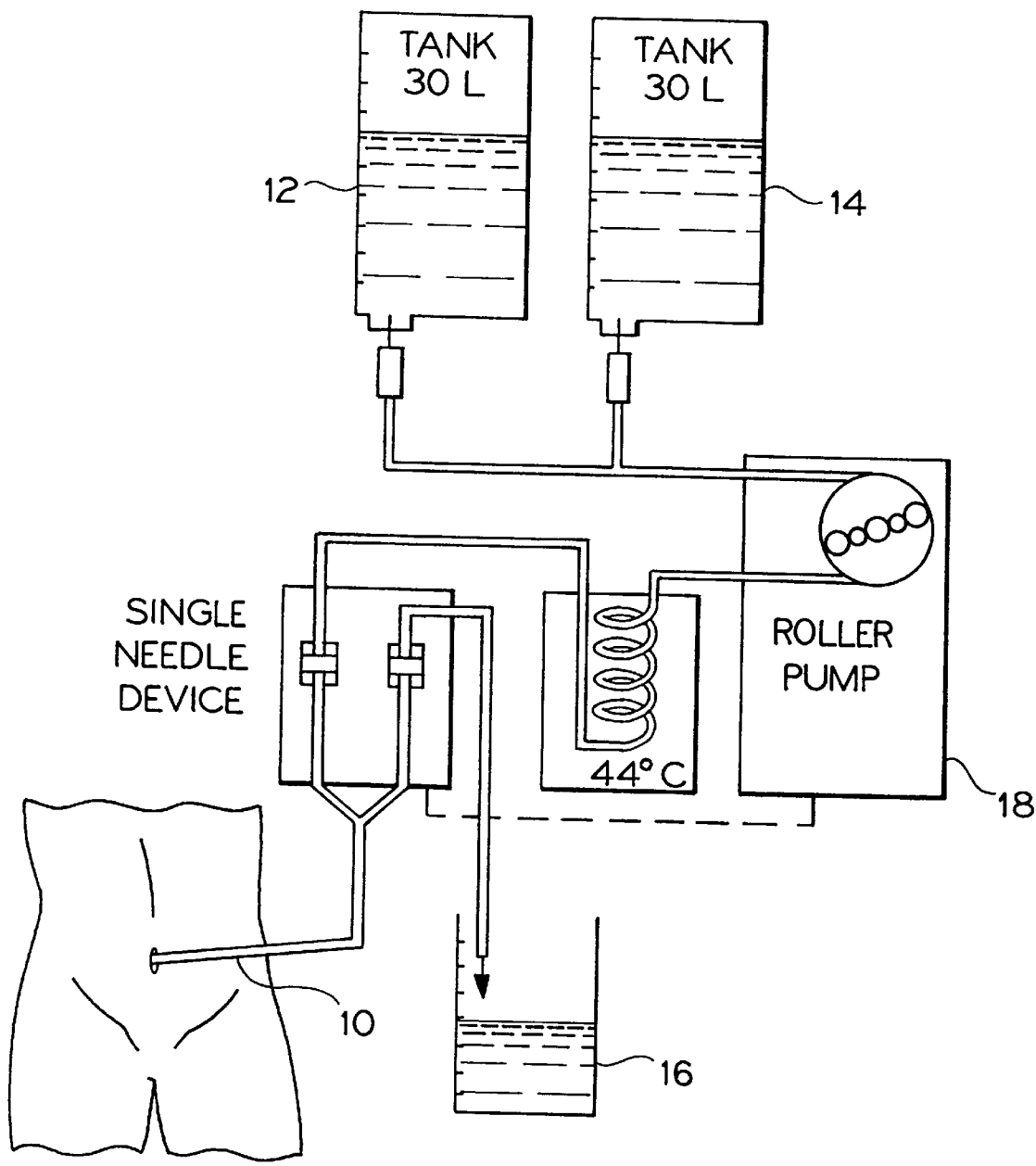
FIG. 1 illustrates, schematically, a prior art peritoneal dialysis system.
Figure 2:
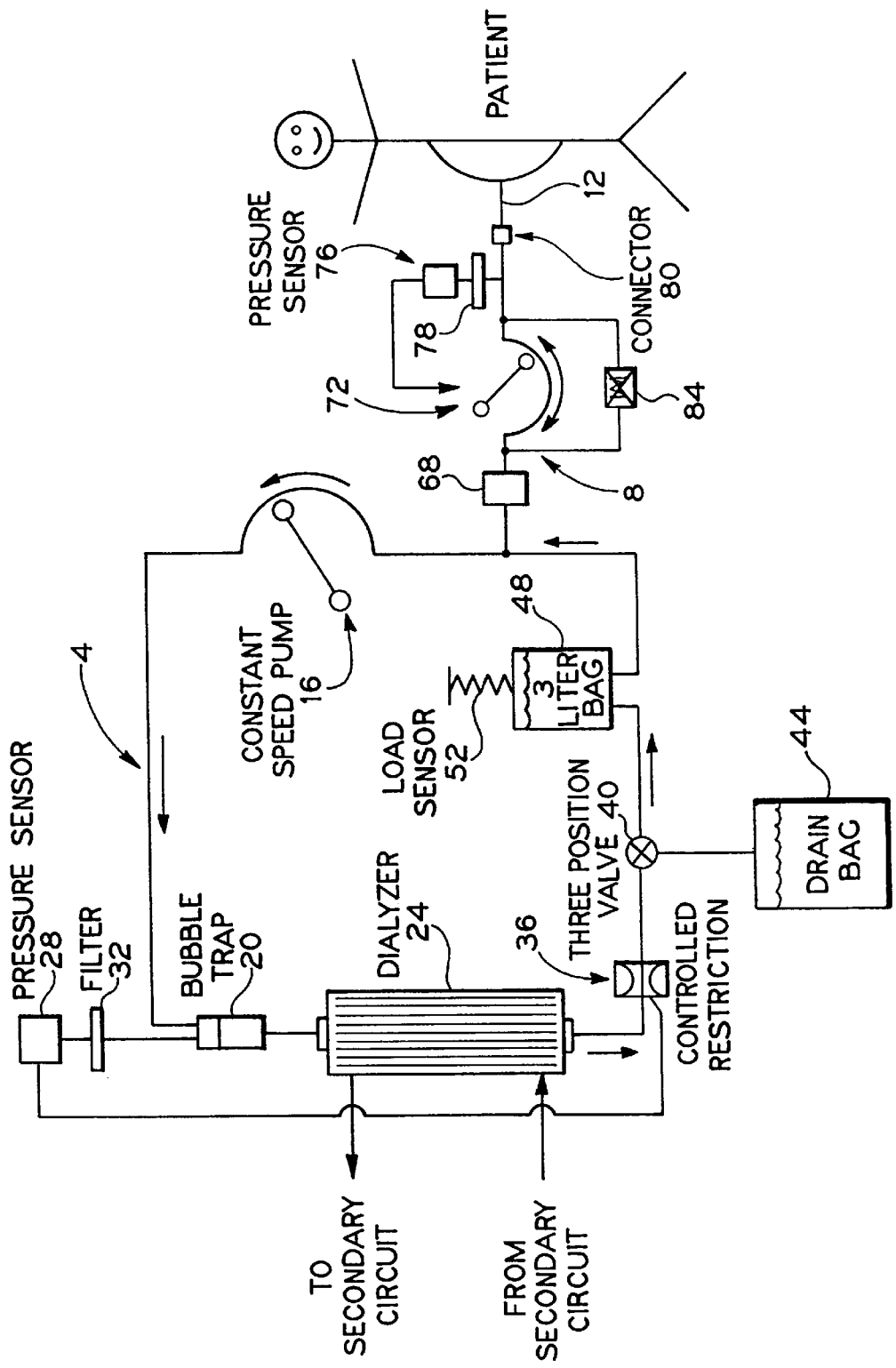
FIG. 2 illustrates, schematically, another prior art peritoneal dialysis system.
Figure 3:
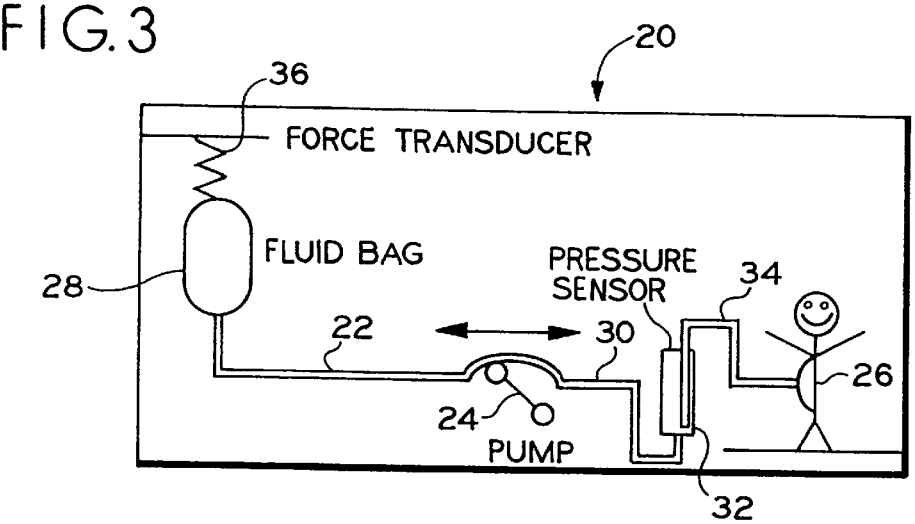
FIG. 3 illustrates, schematically, an embodiment of the system of the present invention.

Referring now to FIG. 3, as illustrated, the present invention provides a system 20 that includes a fluid circuit 22 and a single pump 24. The single pump 24 is used to pulse fluid into and out of the peritoneal cavity of the patient 26. Unlike the prior art methods that required multiple pumps and circuits that resulted in complicated systems that are difficult to set up and are expensive, the present invention provides a single fluid circuit that requires only a single pump 24.

The system 20 also includes a reservoir 28. The reservoir 28 contains the dialysate that is to be administered to the patient. The dialysate can be any peritoneal dialysis solution desired. Preferably, the reservoir 28 has a volume of at least one and one half times the patient's fill volume, e.g., greater than or equal to three liters. In a preferred embodiment, the reservoir 28 has a volume of at least five liters.

The reservoir 28 of the present invention is used to help maintain the diffusive gradient. The reservoir 28 participates in peritoneal transport as if it were part of the peritoneal cavity. As a result given a two liter initial fill and a three liter or more reservoir it appears as if five or more liters have been infused into the patient. With prior systems, the reservoir size is not integral to the therapy and merely serves to hold the stroke volume prior to reinfusion. In contrast, the reservoir 28 in the present system acts as the principal means of maintaining the diffusive gradient.

The current system is more efficient than multiple infusions since the inflow and outflow processes are eliminated. The advantage over normal peritoneal dialysis comes from the fact that no "down time" due to filling and emptying the peritoneal cavity exists. Consequently, seven liters, for example, of the fluid in the system of the present invention will dwell longer and come closer to equilibrium than seven liters of fluid in normal peritoneal dialysis.

Moreover, maintaining the diffusive gradient by having a larger than normal volume available to the peritoneal membrane coupled with the augmentation of transport due to the high flow results in even faster equilibration. Thus, the same therapy achieved in normal peritoneal dialysis can be obtained in less time with a smaller volume of dialysis fluid. Moreover, more therapy can be obtained in the same length of time or even further more therapy can be obtained in a given time with a smaller volume of dialysis fluid.

Fluid (dialysate) is moved into and out of the patient by use of the single pump 24. In the embodiment illustrated, the pump is a reversible roller pump 24. The pump 24 is positioned to act on a fluid line 30 that extends from an end of the reservoir 28 to a pressure detection system 32. A further line 34 extends from the pressure detection system 32 to the patient 26.

Figure 5:
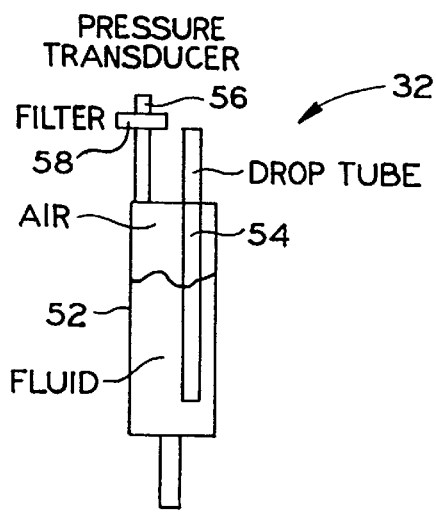
FIG. 5 illustrates, schematically, the pressure detection system of the embodiment shown in FIG. 3. However, a preferred embodiment of the invention does not require this system.
Figure 6:
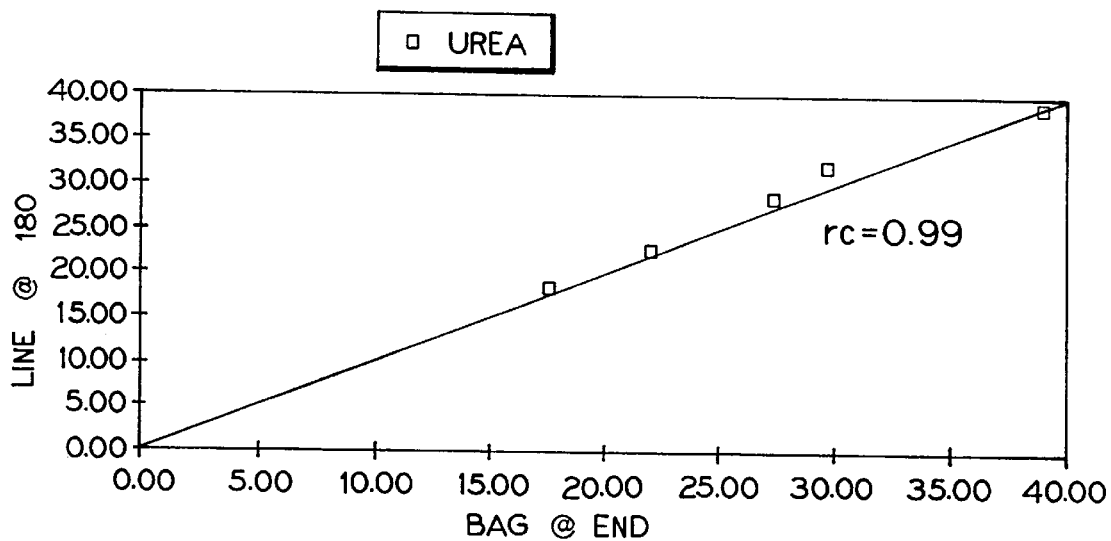
FIG. 6 graphically illustrates results for a sample of the end of therapy concentration in the reservoir bag versus 180 minute sample taken from the tidal oscillating pulse peritoneal dialysis line.
Figure 7:
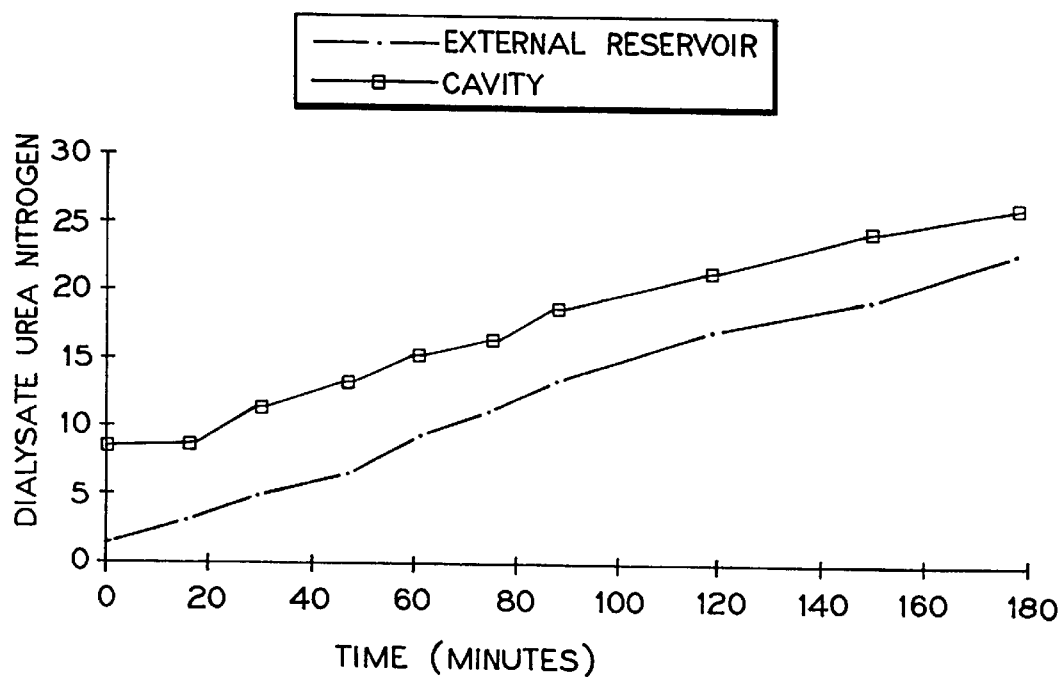
FIG. 7 illustrates the change in concentration as a function of time for the cavity (upper line) and for the external reservoir (bottom line). The parallel increase in concentration shown by the two lines indicate that the external reservoir and the cavity participate equally in the exchange.

FIG. 5 illustrates the pressure detection system 32 of the present invention. The pressure detection system 32 includes a drip bulb 52. The drip bulb 52 permits an air/water interface to be formed as shown in FIG. 5. The drip bulb 52 includes a longer than normal drop tube 54. The drop tube 54 reaches deep into the drip bulb 52, allowing fluid to flow in both directions without air being introduced into the system.

A pressure transducer 56 measures the pressure of the air that is at the fluid line pressure. A number of fluid pressure transducers are suitable for use in the system of the present invention. For example, a Cole-Palmer G-68801-53 diaphragm-type pressure sensor can be used in the present invention. A disposable plastic filter 58 separates and protects the pressure transducer 56 from the fluid. The disposable plastic filter 58 consists of a hydrophobic material that only permits air to pass through to the pressure transducer 56, thus necessitating the air/water interface. Naturally, if the membrane used in the disposable plastic filter 58 was impermeable and flexible (i.e. condom-like), no air/water interface would be necessary.

Fluid line 34 terminates at a catheter (not shown) that is in fluid communication with the peritoneal cavity of the patient 26. The pump 24 can cause fluid to move in either direction through the fluid circuit 22 of the system 20.

Pursuant to the present invention, by use of the pump 24, the fluid (dialysate) can be transported via small stroke volumes. By way of example, the small stroke volume can be roughly four to five times the dead space of the tubing, of fluid line 34, and less than 15% of the total fill volume. The small stroke volumes allow fluid to be moved at high flow rates (400 ml/min) both into and out of the patient 26 without causing discomfort to the patient 26.

Pursuant to the present invention, stroke volumes are smaller (approximately 300 ml or less) than in prior art systems. Since only a small portion of the cavity is emptied, fluid can be pumped out at a high flow rate (≈400 ml/min) without sucking omentum into the catheter. This provides, among other things, for a greater mixing in the peritoneal cavity by breaking up stagnant fluid layers in the cavity.

The high flow rates also decrease blockage within the system. When blockages do occur, due to omentum or fibrin, the pressure transducer 54 senses a change (increase/decrease) in pressure. As a result, the pump 24 shuts off sounding an alarm. After corrective action is taken, the pump 24 again resumes pumping.

In the embodiment illustrated in FIG. 3, a force transducer 36 measures the amount of fluid that is pumped into the patient 26. The reservoir 28 is hung from the force transducer 36. An example of such a force transducer is an Omega LCB-50 Bending Beam Load Cell. As discussed below, with reference to FIG. 4, the force transducer 36 is not required for certain embodiments of the present invention. Likewise, in certain embodiments, the pressure transducer 54 is not required.

Pursuant to the present invention, standard bags of sterile dialysis can be used to prime the circuit. The priming of the circuit eliminates the need for a fluid sterilizing chamber. To prime the system, the following procedure can be followed.

A sterile connection is made between a sterile source bag of fluid (3000 ml or greater) and the sterile line set. The line set consists of a piece of sterile tubing with a spike on one end to fit into a bag and a patient connector on the other end to hook to a patient's transfer set. When using a roller pump, this also includes a "pump segment" which is a larger tubing segment that fits into the reversible roller pump. It may also include provisions for line pressure monitoring. For instance, a "drip bulb" where there is an air and water interface may be used. The air interface connects to a pressure transducer through a 0.22μ membrane (which excludes viruses and bacteria). Also included is a plastic clamp to start and stop the flow. The bag is raised, the clamp is released and sterile fluid enters the line set. The drip bulb is inverted so it is filled. The fluid flows to the end of the line set and the clamp is reclamped. After this procedure is completed, the line set is connected to the patient 26 who is then filled with dialysate.

Figure 4:
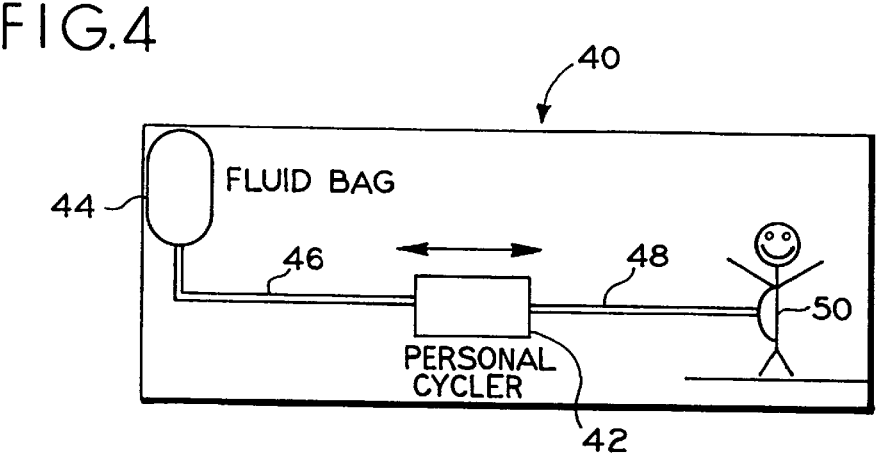
FIG. 4 illustrates, schematically, another embodiment of the system of the present invention.

Referring now to FIG. 4, another embodiment of the present invention is illustrated. FIG. 4 illustrates a system 40. In this embodiment, rather than utilizing a reversible roller pump, as used in the embodiment of the invention illustrated in FIG. 3, a personal cycler 42 can be utilized.

"Personal cycler", as that term is used in the present application, refers to a pressure driven, diaphragm-type volumetric displacement pump. The personal cycler 42 can determine the volume of liquid delivered as the difference in the volume of a pumping chamber before and after a pumping stroke. The pumping chamber consists of two parts separated by a flexible diaphragm with air on one side and fluid on the other. Increasing the air pressure pushes liquid out of the chamber expanding the volume on the air side.

The personal cycler 42 measures the pressure on the air side of the diaphragm and the pressure in a known standard volume before and after the pumping chamber is connected to the standard volume. Based on these measurements, the personal cycler 42 can determine the amount of fluid delivered. The formula for such measurements is as follows:

$$V_{delivered} = V_{filled} - V_{empty} = [(P_{s1} - P_{s2}) * V_s / (P_{d2} - P_{d1}]_{filled} - (SP_{s1} - P_{s2}) * V_s / (P_{d2} - P_{d1}]_{empty}$$

where "1" refers to the pressure before the air side of the diaphragm is connected to the standard volume where "2" refers to the pressure after the air side of the diaphragm is connected to the standard volume "s" refers to the standard volume "d" refers to the air side of diaphragm.

Examples of a personal cycler are disclosed in U.S. applications: "Peritoneal Dialysis Systems and Methods Employing a Liquid Distribution and Pumping Cassette That Emulates Gravity Flow", filed Mar. 3, 1993, Ser. No. 08/027,328; "Peritoneal Dialysis Systems and Method Employing a Liquid Distribution and Pump Cassette with Self-Contained Air Isolation and Venting", filed Mar. 3, 1993, Ser. No. 08/027,484; "Liquid Pumping Mechanisms for Peritoneal Dialysis Systems Employing Fluid Pressure", filed Mar. 3, 1993, Ser. No. 08/027,485; "Peritoneal Dialysis Systems and Methods Employing Pneumatic Pressure and Temperature-Corrected Liquid Volume Measurements", filed Mar. 3, 1993, Ser. No. 08/026,458, "Improved User Interface and Monitoring Functions for Automated Peritoneal Dialysis Systems", filed Mar. 3, 1993, Ser. No. 08/025,531; "Improved User Interface for Automated Peritoneal Dialysis Systems", filed Mar. 3, 1993, Ser. No. 08/025,547; and "Peritoneal Dialysis Cycler", filed Mar. 3, 1993, Ser. No. 29/006,426, the disclosures of all of which are incorporated herein by reference.

Pursuant to this embodiment of the invention, a reservoir bag 44 provides the dialysate. Fluid (dialysate) flow is through fluid line 46 through the personal cycler 42. A second end of the personal cycler 42 is coupled to the patient 50 by fluid line 48 that terminates at a catheter in fluid communication with the patient's peritoneal cavity.

A personal cycler 42 affords fluid flow into and out of the patient. Similar to the pump of FIG. 3, the personal cycler 42 allows fluid to flow in either direction of the fluid circuit.

In this alternative embodiment, utilizing a personal cycler 42 eliminates the need for a pressure sensor and a force transducer. Because the personal cycler 42 is a pressure driven volume displacement pump, fluid can be precisely metered without an external pressure sensor being required. Pressure driven means that the output pressure does not exceed the pressure applied to the diaphragm that pumps the fluid. As a result thereof, no need exists to protect the patient from higher pressures using a separate pressure sensor. Likewise, because the personal cycler 42 directly senses the pressure, safety pressure transducers, utilized in the embodiment illustrated in FIG. 3, are not required.

Naturally, the priming procedure for this alternate embodiment differs from the embodiment illustrated in FIG. 3. In this embodiment, the patient acts as his/her own prime. An empty line set and cassette is connected to the patient and one line is connected to a filled 5 liter bag on the heating plate of the personal cycler 42. The patient is emptied until only residual fluid remains in the lines. This is then reinfused along with 2 liters of new fluid.

The 5 cassette lines will be assigned as follows: 1 line will connect to the patient; 1 line will go to the drain; the remaining three lines will be connected to 5 liter bags of fluid—two of these will be on the heating plate. The remaining bag will act as a "last fill" and an "initial fill." After the patient is emptied, he/she will be filled with 2 liters of fluid from one of the bags on the heater and this same bag will be simultaneously replenished (the personal cycler 42 has two pumping chambers) with cold fluid. Then with 2 liters inside the patient and 5 liters external to the patient, fluid will be moved back and forth between one of the heater bags and the patient for some duration (e.g. 4 hours). At the end of this time, cycling will occur between the patient and the second heated 5 liter bag for another given duration (e.g. 4 hours). Then the patient will be emptied and refilled with the remaining unused fluid.

The inventors have also discovered that vibrating the reservoir containing the dialysate when performing dialysis effectively increases the dialysis efficiency. In general, peritoneal dialysis is a repetition of injecting a dialytic liquid into an abdominal cavity. The contact between the dialytic liquid and the blood sets up a concentration gradient which causes the extraction of impurities within the blood into the dialytic liquid via diffusion. The osmotic pressure difference results in ultrafiltration which is the removal of water from the body.

Accordingly, the dialytic liquid and the blood are in contact with each other through the peritoneum. However, since a so-called channeling phenomenon causes the dialytic liquid to flow in a particular passage, the contact area is limited. In addition, a tendency of partial circulation of the dialytic liquid in the direction of the hypogastric region further limits the contact area. Due to this limited contact area, the dialysis efficiency does not increase as expected.

The inventors have discovered that using vibration can increase the dialysis efficiency. In an embodiment, the system further includes means for physically vibrating the reservoir containing the dialysate during dialysis. As those skilled in the art will realize, a number of ways exist to apply vibration to the reservoir. For instance, a traditional vibrator or an electric massager may be utilized.

The parameters of the equipment utilized to apply vibration vary depending on the dialysis progress. In an embodiment, the frequency of vibration is a low frequency ranging from 1 to 30 Hz. While this frequency provides effective results, those skilled in the art will appreciate that ranges falling outside this range will also produce effective results. The direction of vibration may naturally be adjusted accordingly to the dialysis progress.

It should also be appreciated that the vibration of the abdomen will increase not only the efficiency of tidal oscillating pulse peritoneal dialysis but also other peritoneal dialysis methods.

By way of example, and not limitation, experiments illustrating the invention will now be given.

Experiment No. 1

In this experiment, five patients (4 female, 1 male) of varying transport types were run on the tidal oscillating pulse peritoneal dialysis system (TOPPD) of the present invention for three hours preceded and followed by a standard 90 minute dwell. Fluid (dialysate) was cycled between the peritoneal cavity and a reservoir having a volume of 5 liters via a reversible peristaltic pump. Dialysate samples were taken every 15 minutes from the patient's cavity and from the external reservoir during these procedures. Blood samples were taken at the beginning and the end of each procedure.

To determine the efficiency of the procedure, compartmental modeling was employed to obtain the effective mass transfer area coefficients (MTAC) for the 90 minute dwell and the TOPPD procedure. This allows the procedures to be compared since the effects of fluid quantity, and treatment time are eliminated.

In this experiment, the inventors found that TOPPD provided a MTAC augmentation in one patient of 13% for urea and in two patients 25–40% for creatinine. No or minimal MTAC augmentation was found in 3 of the 5 patients. The data suggests that TOPPD may be efficacious in some patients but will have little or no effect on MTAC in others, although the elimination of drain and fill time will still increase efficiency by around 10% compared to normal nightly peritoneal dialysis.

Table 1 below shows this data. Table 1 illustrates the MTAC augmentations (in percent) via the compartmental modeling method referred to above. Augmentations were calculated as the MTAC of TOPPD divided by the average of the MTACs from the two 90 minute dwells.

TABLE 1

| Patient ID | Aug Urea | Aug Crtn |
|---|---|---|
| #6 | 13.9 | 36.7 |
| #7 | 1.1 | 22.0 |
| #8 | −24.3 | −19.3 |
| #9 | −9.1 | −4.1 |
| #10 | −3.8 | 0.0 |

Although the Table shows some negative augmentations, these should not be interpreted as changes in the intrinsic properties of the peritoneal membrane. The negative augmentation in the case of patient #8 was attributed to catheter malpositioning while the slight decreases noted in the case of patients #9 and #10 are probably measurement artifacts so that the actual augmentation is close to zero. This illustrates that while better mixing can be obtained in some patients (e.g., #6 and #7), there can still be isolated fluid pockets which do not fully participate in the exchange (e.g., #8). By increasing the stroke volume and/or changing the catheter position, these pockets can be eliminated and transport increased. Also despite potential decreases in MTAC, the therapy still gains efficiency from the decreased fill and drain time.

Notably, these augmentations were attainable with a flow rate of 400 ml/min. Preferably, the target platform for TOPPD is the Home Choice™ Baxter personal cycler. The personal cycler has a pulsatile waveform approaching 400 ml/min at slightly higher than normal actuation pressures. Despite the fact that the average flow rate does not conceivably exceed 270 ml/min, conceivably the augmentation noted above could be attainable without appreciable modification of the hardware base.

Experiment No. 2

This experiment examines the ability to increase dialysis efficiency by applying physical vibration to a reservoir containing dialysate.

The experiment examines the effect on 5 adult dogs (10–13 kg). Each dog was anesthetized with nembutal and received a laparotomy. The omentum was removed and a Tenckhoff catheter and a catheter for monitoring intraperitoneal pressure (IPP) were retained. A cannula was inserted into the femoral artery for blood pressure measuring and blood sampling.

Dialysis

Control 1000 ml of Dianeal® 2.5% was instilled in the abdominal cavity.

Extracorporeal Pulsatile Peritoneal Dialysis (EPPD)

1000 ml of Dianeal® 2.5% was instilled in the abdominal cavity and a bag which contained 1000 ml of Dianeal® 2.5% was connected to the retained Tenckhoff catheter (Total 2000 ml dialysate). The connection between the abdominal cavity and the bag was kept open. An electric massager attached to the bag pulsated the bag. Two pulse cycles were tested, 150 cycles/min on two dogs and 1440 cycles/min on three dogs, during the cycles the effects of the pulsation on the efficacy of peritoneal dialysis were examined.

Observations

Urea, creatinine, inulin and dextran 70 were added in the dialysate. Blood pressure, IPP, UFR, and the concentration of the added substances were monitored every 30 minutes for 120 minutes. The measurement of "dialysance" was performed by the number of milliliters of peritoneal fluid completely cleared of all substances and transferred into the blood.

Results

UFR, Dialysance

UFR increased (1.0 vs 1.75 ml/min) but no significant change in dialysance was observed with 150 cycle/min EPPD compared to the control.

During treatment with 1440 cycle/min EPPD, the dialysance of the UN, creatinine and glucose increased by 10%, 42%, 59% on average, respectively, and UFR increased by 84%. Table 2 below illustrates these results.

TABLE 2

| | UFR | dialysance(ml/min) | | |
|---|---|---|---|---|
| | (ml/min) | UN | CRTN | glucose |
| cont PD | 1.02 | 8.06 | 3.72 | 2.85 |
| EPPD | 1.88 | 9.50 | 5.29 | 4.54 |

IPP

IPP changed from 2 to 7 mmHg through the use of pulsation. However, there was no significant difference in the average IPP between EPPD and control (EPPD 5.0 mmHg, control 4.5 mmHg).

It should be understood that various changes and modifications to the presently preferred embodiments described herein will be apparent to those skilled in the art. Such changes and modifications can be made without departing from the spirit and scope of the present invention and without diminishing its attendant advantages. It is therefore intended that such changes and modifications be covered by the appended claims.

We claim:

1. A system for providing peritoneal dialysis to a patient comprising:
   a fluid catheter having a first end adapted to be placed in a peritoneal cavity of a patient having an associated peritoneal cavity fill volume and a second end directly connected to a fluid line, the fluid line connecting the second end of the catheter to a dialysate reservoir container containing a volume of dialysate fluid at least about one and one-half times the cavity fill volume, and a single pump for reversibly pumping dialysate fluid along the fluid line from the reservoir container to the fluid catheter and into the patient's peritoneal cavity and from the patient's patient's peritoneal cavity through the fluid catheter and along the fluid line directly back into the reservoir container, whereby after an initial volume of dialysate fluid is introduced into the patient's peritoneal cavity, smaller volume portions less than the initial volume of dialysate fluid may be periodically and successively removed from the patient's peritoneal cavity and returned directly to the reservoir container to dilute dialyzed waste products from the patient and portions of the dialysate fluid present in the reservoir container may be introduced into the patient's peritoneal cavity to maintain a diffusive gradient and provide peritoneal dialysis to the patient.

2. The system of claim 1 further including a force transducer coupled to the dialysate reservoir container for monitoring the amount of dialysate fluid pumped into the patient.

3. The system of claim 1 wherein the pump is a reversible roller pump.

4. The system of claim 1 wherein the pump is a personal cycler.

5. The system of claim 1 further including a pressure detection system in fluid communication with the pump.

6. The system of claim 1 further including means for physically vibrating the dialysate reservoir container during dialysis.

7. A method for dialyzing a patient comprising the steps of:

providing a fluid catheter having a first end adapted for placement in a peritoneal cavity of a patient having an associated peritoneal cavity fill volume and having a second end directly connected to a fluid line, the fluid line connecting the second line of the catheter to a dialysate reservoir container containing a volume of dialysate fluid at least about one and one-half times the cavity fill volume;

placing the first end of the catheter in the peritoneal cavity of the patient;

introducing an initial volume of dialysate fluid into the patient's peritoneal cavity less than or equal to the cavity fill volume;

periodically pumping a smaller volume of dialysate fluid less than the initial volume from the patient's peritoneal cavity directly back into the reservoir container for dilution with remaining dialysate fluid present in the reservoir container and pumping a volume of dialysate fluid from the reservoir container into the patient's peritoneal cavity to maintain a diffusive gradient until a desired amount of dialysis has been achieved and thereafter, removing dialysate fluid from the patient's peritoneal cavity.

8. The method of claim 7 including coupling the dialysate reservoir container to a force transducer for monitoring the amount of dialysate fluid pumped into the patient.

9. The method of claim 7 wherein the step of pumping the dialysate fluid is further defined by using a reversible roller pump for pumping the dialysate fluid.

10. The method of claim 7 wherein the step of pumping the dialysate fluid is further defined by using a personal cycler for pumping the dialysate fluid.

11. The method of claim 7 including placing a pressure detection system in fluid communication with the pump.

12. The method of claim 7 wherein the volume of dialysate fluid is at least five liters.

13. The method of claim 7 including the further step of applying physical vibration to the dialysate reservoir container when pumping the dialysate fluid into and out of the peritoneum.

* * * * *